(12) United States Patent
Kumar (10) Patent No.: US 7,740,794 B1
(45) Date of Patent: Jun. 22, 2010

(54) METHODS OF MAKING A POLYMER AND CERAMIC COMPOSITE

(75) Inventor: Mukesh Kumar, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1440 days.

(21) Appl. No.: 11/108,657

(22) Filed: Apr. 18, 2005

(51) Int. Cl.
C04B 33/32 (2006.01)

(52) U.S. Cl. ................................... 264/626; 264/627

(58) Field of Classification Search .............. 264/626, 264/627; 501/95.1, 134
See application file for complete search history.

(56) References Cited

U.S. PATENT DOCUMENTS

| | | | |
|---|---|---|---|
| 4,612,923 A | 9/1986 | Kronenthal | |
| 4,655,777 A | 4/1987 | Dunn et al. | |
| 4,743,256 A | 5/1988 | Brantigan | |
| 4,834,754 A | 5/1989 | Shearing | |
| 4,863,472 A | 9/1989 | Törmälä et al. | |
| 4,878,915 A | 11/1989 | Brantigan | |
| 4,904,261 A | 2/1990 | Dove et al. | |
| 4,976,736 A | 12/1990 | White et al. | |
| 5,059,209 A | 10/1991 | Jones | |
| 5,192,327 A | 3/1993 | Brantigan | |
| 5,306,309 A | 4/1994 | Wagner et al. | |
| 5,425,772 A | 6/1995 | Brantigan | |
| 5,433,751 A | 7/1995 | Christel et al. | |
| 5,626,861 A | 5/1997 | Laurencin et al. | |
| 5,645,596 A | 7/1997 | Kim et al. | |
| 5,702,449 A | 12/1997 | McKay | |
| 5,728,159 A | 3/1998 | Stroever et al. | |
| 5,766,618 A | 6/1998 | Laurencin et al. | |
| 5,776,199 A | 7/1998 | Michelson | |
| 5,865,845 A | 2/1999 | Thalgott | |
| 5,989,289 A | 11/1999 | Coates et al. | |
| 6,039,762 A | 3/2000 | McKay | |
| 6,077,989 A | 6/2000 | Kandel et al.. | |
| 6,139,585 A | 10/2000 | Li | |
| 6,143,033 A | 11/2000 | Paul et al. | |
| 6,187,047 B1 | 2/2001 | Kwan et al. | |
| 6,203,574 B1 | 3/2001 | Kawamura | |
| 6,241,771 B1 | 6/2001 | Gresser et al. | |
| 6,281,257 B1 | 8/2001 | Ma et al. | |
| 6,283,997 B1 | 9/2001 | Garg et al. | |
| 6,296,667 B1 | 10/2001 | Johnson et al. | |
| 6,323,146 B1 | 11/2001 | Pugh et al. | |
| 6,331,312 B1 | 12/2001 | Lee et al. | |
| 6,340,648 B1 | 1/2002 | Imura et al. | |
| 6,371,988 B1 | 4/2002 | Pafford et al. | |
| 6,406,498 B1 | 6/2002 | Törmälä et al. | |
| 6,447,544 B1 | 9/2002 | Michelson | |
| 6,458,162 B1 | 10/2002 | Koblish et al. | |
| 6,503,278 B1 | 1/2003 | Pohjonen et al. | |

(Continued)

OTHER PUBLICATIONS

University of Nebraska Lincoln, "Polymerization of Lactide and Glycolide Using Solid State Initiator," Dr. Dipanjan Nag.

*Primary Examiner*—Carlos Lopez
(74) *Attorney, Agent, or Firm*—Harness, Dickey (57) ABSTRACT

A method of forming a polymer/ceramic composite for use in various purposes. For example, the polymer/ceramic composite may be used in orthopedic procedures for replacing bone material, forming an implant, providing an anchor or other appropriate uses. The polymer/ceramic composite may also include selected characteristics such as a hardness, a strength, a bioabsorbability, a biocompatibility or other appropriate characteristics.

29 Claims, 4 Drawing Sheets

U.S. PATENT DOCUMENTS

| | | |
|---|---|---|
| 6,503,279 B1 | 1/2003 | Webb et al. |
| 6,524,345 B1 | 2/2003 | Välimaa et al. |
| 6,530,955 B2 | 3/2003 | Boyle et al. |
| 6,673,075 B2 | 1/2004 | Santilli |
| 6,676,703 B2 | 1/2004 | Biscup |
| 6,726,722 B2 | 4/2004 | Walkenhorst et al. |
| 6,731,988 B1 | 5/2004 | Green |
| 6,733,535 B2 | 5/2004 | Michelson |
| 6,736,849 B2 | 5/2004 | Li et al. |
| 6,863,899 B2 | 3/2005 | Koblish et al. |
| 2002/0037799 A1 | 3/2002 | Li et al. |
| 2002/0127391 A1* | 9/2002 | Kumar ........................ 428/325 |
| 2003/0167093 A1 | 9/2003 | Xu et al. |
| 2003/0233147 A1 | 12/2003 | Nicholson et al. |
| 2004/0002770 A1 | 1/2004 | King et al. |
| 2004/0093089 A1 | 5/2004 | Ralph et al. |
| 2005/0070905 A1 | 3/2005 | Donnelly et al. |

* cited by examiner

METHODS OF MAKING A POLYMER AND CERAMIC COMPOSITE

FIELD

The present invention relates generally to a biocompatible material for use in an anatomy, and particularly relates to a bioabsorbable composite material for use in orthopedic procedures.

BACKGROUND

Although various procedures and materials may be used to perform orthopedic procedures, it may be useful to provide a bioabsorbable or biocompatible material formed of a plurality of materials. For example, various materials may include a selected characteristic while a second material may include a complimentary characteristic. Nevertheless, these various materials may be generally separate, although it may be useful to provide them in a single location.

Various materials, such as bone cement, bioabsorbable polymers, ceramics, and the like, each provide various characteristics or advantages for a selected procedure. Nevertheless, it may be desirable to provide more than one of these properties at a selected location. For example, it may be desirable to provide a bioabsorbable polymer that has a selected strength or wear characteristic, such as that similar to a ceramic. Providing a volume of both a polymer and a ceramic, however, in a single selected location may not be feasible.

For example, an attempt to provide both a polymer and a ceramic, such as a polymer surrounding a ceramic may be used. Various attempted methods include using a ceramic pre-form or a plurality of particles in a selected orientation that can be positioned in a mold or that may form a part of a mold for infiltration with a polymer. Forming such polymer/ceramic composite is difficult, especially in selected orientations. Positioning a ceramic in a mold and injecting a selected polymer therein may increase the complexity of the formation of the material and reduce the possible configurations of the final product.

SUMMARY

Various methods and materials for forming a polymer/ceramic composite is disclosed. The composite may be directly molded into a selected configuration or implant, such as a bone replacement prosthesis or other appropriate implant. Methods, according to various embodiments, may include forming a blank by precipitating a dissolved polymer around a selected ceramic particle or to incorporate a ceramic particle. Various embodiments also include polymerizing various materials, such as components or monomers, with a ceramic particle suspended in the polymerization bath. Therefore, the polymerized product can include the ceramic material trapped therein. Also, the selected polymer may be melted and resolidified around a selected ceramic particle. The polymer may be melted in a substantially nondegrading way, such that various characteristics may be maintained in the final product, to include the ceramic particle.

The polymer/ceramic composites or complex may then be used for various purposes. For example, the polymer/ceramic composite may be used as a bone filling material or volume: To replace bone that is removed due to degeneration, resection, or other issues. The polymer/ceramic composite may also be used to form selected implants, such as screws, suture or soft tissue anchors, spacers for spine, vertebral implants, bone plates, or the like. Nevertheless, the polymer may be formed of a substantially bioabsorbable or biocompatible material and the ceramic may also be substantially biocompatible or bioabsorbable. Therefore, when the polymer/ceramic composite is substantially bioabsorbable, the entire prosthesis may be formed to be absorbed into an anatomy, such as a human anatomy, at a selected rate. Therefore, the implant may be implanted and then replaced with a natural anatomical material, such as bone. Nevertheless, the characteristics of the polymer and the ceramic may be applied in a substantially single location for various purposes, such as those discussed herein.

Further areas of applicability of the disclosure will become apparent from the description provided hereinafter. It should be understood that the description and various examples, while indicating various embodiments, are intended for purposes of illustration only and are not intended to limit the scope of the disclosure.

BRIEF DESCRIPTION OF THE FIGURES

The present teachings will become more fully understood from the detailed description and the accompanying figures, wherein.

DETAILED DESCRIPTION OF VARIOUS EMBODIMENTS

The following description of various embodiments is merely exemplary in nature and is in no way intended to limit the present disclosure, its application, or uses. Although the following description may relate generally to forming a bioabsorbable polymer/ceramic composite, it will be understood the polymer/ceramic composites of various compositions may be formed according to the various embodiments described herein. Although a bioabsorbable polymer formed as a composite with a bioabsorbable ceramic may be used for various purposes, it may be desirable for other purposes to provide a nonabsorbable material or combination. For example, a nonabsorbable ceramic may be used with an absorbable polymer to be used for various reasons. Further, it will be understood that various substances, such as antibiotics or other medicines may be carried in the polymer or may be coated in the composite for various purposes.

Figure 1:
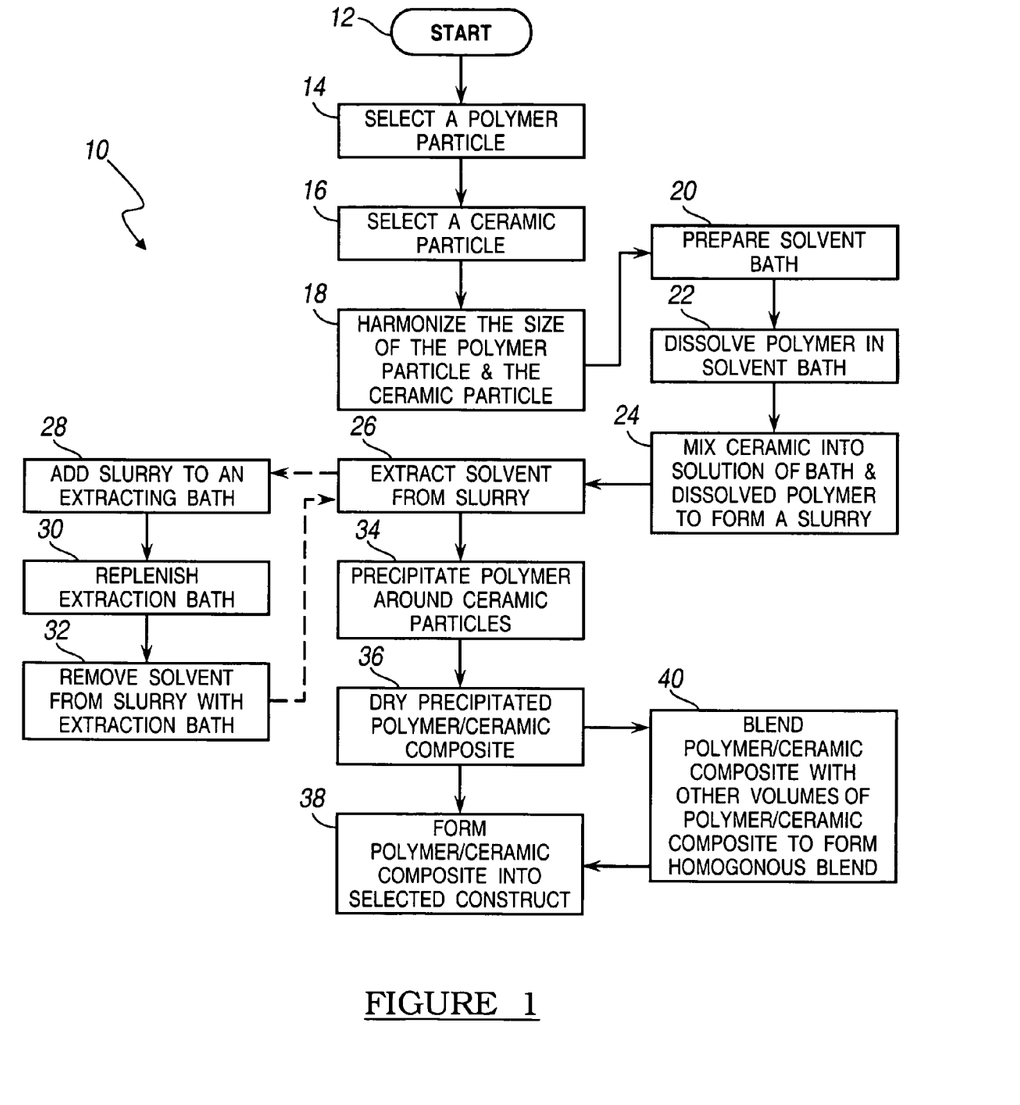
FIG. 1 is a diagrammatic flow chart for forming a polymer/ceramic composite according to various embodiments.

With reference to FIG. 1, a flow chart illustrates a method 10 for forming a polymer/ceramic composite. The composite may be used for various purposes, such as those described herein. Generally, the polymer may be formed around or to incorporate a selected volume of ceramic particles for use in a procedure, such as a bone replacement procedure or any appropriate implant. The method 10 generally starts in block 12. A polymer particle may then be selected in block 14. The polymer particle may be any appropriate particle or form of a polymer, such as a polylactic acid, such as Lactosorb®, marketed by Biomet, Inc., although any other appropriate biocompatible polymer or combination of polymers can be used. The polymer is generally formed in particles of a selected size, which may be appropriate for various procedures, such as injection molding, casting, and the like. Regardless, the polymer particles may generally be formed in various shapes or sizes for selected procedures. The polymer particles selected in block 14 may either be preformed or ground to a selected size. For example, the polymer particles may generally be about 500 to about 1000 microns as measured by appropriate methods known to those skilled in the art. It may be selected, however, to form the particles to a size of about 200 to about 400 microns. Therefore, the polymer particles selected in block 14 may be ground to a selected size for various purposes. For example, as discussed herein, the particle size of the polymer may be formed to be similar to the particles size of the ceramic. Again the polymer selected in block 14 may be biocompatible and can be either resorbable or non-resorbable.

After the polymer is selected in block 14, a ceramic particle may be selected in block 16. The ceramic particle selected in block 16 may be any ceramic particle. For example, the ceramic may include or be selected from a calcium carbonate, calcium sulfate, tricalcium phosphate, tetracalcium phosphate, other appropriate resorbable ceramic, or combinations thereof. The ceramic may also be any generally inorganic crystalline material, such as various antibiotics or other pharmaceuticals, growth factors, bone particles, or the like. The ceramic may also be a mixture of several different ceramics. The inorganic material can be formed into a crystalline structure and used in place of the ceramic, therefore it will be understood that using a ceramic herein will not be limited to using a fired inorganic material, but may be any appropriate crystalline material. The ceramic may also be a mixture of several different ceramics. Nevertheless, as discussed above, various non-bioabsorbable ceramics may be used. The non-resorbable ceramics may, however, be biocompatible, such as alumina, titanium oxide, or other appropriate biocompatible, but non-resorbable ceramics. It will be understood that various ceramics may include a selected amount of bioabsorption, while not being completely bioabsorbable. Also the ceramic used may include a mixture of both resorbable and nonresorbable ceramics. It will be understood that such ceramics are within the scope of various embodiments described herein and the various examples provided are illustrative only. Regardless, the ceramic particles selected in block 16 may be of any appropriate size. Nevertheless, the ceramic particles may include an average size of about 10 nanometers to about 5000 microns as measured according to appropriate methods known by one skilled in the art. It will be understood, however, that the particles of the ceramics selected at block 16 may be formed to any appropriate particle size or may be obtained in any appropriate particle size. In addition, the ceramic particle may have porosity ranging from 99% to 1%. The ceramic particle may complete about 10% to 95% of a composite, as discussed herein. For example, the ceramic can be about 10% to about 50% of the composite. The amount of ceramic particles can be measured by either weight percent or volume percent according to various procedures.

The particles of the polymer selected at block 14 and the particles of the ceramic selected at block 16 may be optionally harmonized in block 18. It will be understood that harmonizing the particle size of the polymer selected at block 14 and the ceramic selected in block 16 is merely optional and not required. Nevertheless, harmonizing the particles, such as the particle sizes, may assist in the formation of the selected polymer/ceramic composite or complex. Harmonizing the particles will be understood to be any process, method, or system, that allows the particles to be used together to form a selected product or the product to have a selected characteristic.

For example, harmonization may be performed when the polymer particles selected at block 14 are be generally obtained as substantially large or relatively large particles. For example, the particles may be more than about 1000 or several thousand microns long and include a small diameter, thus having a high aspect ratio. A small powder ceramic, such as one having a particle size of tens of microns may not easily mix or easily form the selected composite or complex. Therefore, the size of the particles may be harmonized to assist in forming the selected composite. For example, the particle size of the polymer selected in block 14 may be reduced, such that it is about equal to no more than about fifty times greater than the particle size of the ceramic particle selected in block 16. Nevertheless, it will also be understood that the particle size of the polymer may be formed to be substantially equal to the particle size of the ceramic selected in block 16. The particle sizes may generally be chosen so that the formation of the complex may be achieved according to a selected manner. For example, the harmonization of the particle size may include formation of the polymer particles to about 500 microns or less and mixing with ceramic particles of about 25 microns or less. Such particles sizes may assist in forming the selected polymer/ceramic composite.

Once the particle sizes have been optionally harmonized, a solvent bath or solvent solution may be formed in block 20. The solvent solution formed in block 20 may be any appropriate solvent solution. The solvent solution generally is operable to dissolve or partially dissolve the polymer selected in block 14. The solvent bath, depending upon the polymer selected in block 14, may include various organic or inorganic solvents. For example, if the polymer selected in block 14 is the polymer used to form Lactosorb®, various solvents may include acetone, N-Methylpyrrolidone (NMP), chloroform, or an appropriate mixture thereof. Although it may be understood that various other solvents may be used that are able to dissolve the polymer selected in block 14.

The polymer is then dissolved in the solvent bath in block 22. According to various embodiments, approximately ten grams of the Lactosorb® is dissolved in about 100 ccs of NMP. It will be understood that any appropriate volume of the polymer selected in block 14 may be dissolved in any appropriate volume of solvent of block 22. The volume of the polymer or the volume of the solvent may be dependent upon the type of polymer or the type of solvent or the temperature of the solvent as well. Therefore, it will be understood that one skilled in the art may be able to determine an appropriate volume of the polymer or the solvent.

The solution, including the dissolved or partially dissolved polymer in the solvent bath formed at block 22 may then have the ceramic particles selected in block 16 added or admixed thereto in block 24. The mixture of the ceramic particles into the solution of the dissolved polymer in the solvent bath or solution may form a slurry of the ceramic particles. The formation of the slurry may be dependent upon the type or volume of the polymer dissolved in the solvent and may also be dependent upon the particle size of the polymer. Generally, however, the slurry may include a viscosity formed for ease of further manipulation. Generally, approximately 50 grams of the selected ceramic, such as a tricalcium phosphate ceramic, may be added to the solution. Therefore, the slurry may include approximately 50 grams of the tricalcium phosphate and about 10 grams of the polymer. Nevertheless, as discussed above, the slurry may include any appropriate amount of the selected materials and they may vary depending upon the volume of the composite desired to be made, density, viscosity of the composite or other various considerations.

Once the slurry is made in block 24, the solvent may be extracted from the formed slurry. Extraction of the solvent may precipitate or cause the precipitation of the polymer from the solution. As the polymer precipitates, the ceramic will be held within the precipitated polymer. As the polymer precipitates from the solution, it may form or solidify around the granules or particles of the ceramic.

The extraction of the solvent from the slurry may be performed according to any appropriate procedure. An exemplary procedure may include the procedure illustrated in blocks 28, 30 and 32. It will be understood that any appropriate extraction process may be used and the exemplary extraction process of blocks 28-32 is not intended to be limiting.

Nevertheless, according to various embodiments, a method of extracting the solvent from the slurry may first include adding the slurry to an extraction bath in block 28. The extraction bath may be any appropriate bath that may extract the solvent from the slurry. For example, the bath may include a water bath, such as a sterile water bath formed according to any appropriate procedure. As the slurry is added to the extraction bath, the solvent is removed from the slurry, which causes the precipitation of the polymer from the slurry. It will be understood that the extraction bath may be any appropriate extraction bath and may vary depending upon the solvent chosen in forming the solvent bath in block 20.

The slurry may be added to the extraction bath in any appropriate method. For example, the slurry may be added dropwise. The slurry may be dripped at a selected rate into the extraction both to cause the extraction of the solvent and the precipitation of the polymer.

According to the exemplary method, the extraction bath may be replenished periodically in block 30. Then the solvent is removed in block 32 according to the extraction method. The extraction method as discussed above is merely exemplary and not intended to limit any appropriate extraction method.

Regardless of the method used to extract the solvent from the slurry in block 26, the polymer is precipitated in block 34. As briefly discussed above, as the polymer precipitates, the polymer is formed around the ceramic particles. In this way, the ceramic particles are formed as a part of the composite or the composite is formed as the polymer forms around the ceramic particles. As discussed above, the density of the particles, such as the ceramic particles, in the composite may depend upon various considerations, such as the volume of the ceramic particles in the slurry or the amount of polymer added to the slurry. Regardless, the precipitated polymer surrounds the ceramic particles to form the composite.

Once the composite has been precipitated, such that the polymer generally surrounds the ceramic particles, the composite may be optionally dried in block 36. The drying of the composite may occur in any appropriate manner, such as in an oven or in a generally air drying manner. Regardless, the drying of the composite will assist in removing the material used in the extraction bath in block 28 and any remaining solvent. This will assist in forming the composite in such a manner that the polymer will include a selected characteristic, such as a viscosity, a polymer chain length, and the like.

Once the precipitated polymer is dried, the composite is generally formed in a manner required for use. Therefore, the precipitated or composite material may be formed into a selected construct in block 38. For example, various implants, prostheses, and the like may be formed with the composite material. As discussed above, the composite material may be used to form a bone replacement, an anchor, such as a suture or soft tissue anchor, or any other appropriate construct.

The composite may be formed into the construct in any appropriate manner. For example, extrusion, injection, pultruding, or any appropriate molding or forming process may be used. Generally, the composite material may be formed substantially or generally similar to a method of forming the polymer into a selected construct or shape by itself. Therefore, generally unique or special manufacturing or processing techniques or methods are not necessary.

Before forming the composite into a selected form, however, it may be chosen to blend a batch of the composite with other batches of the same or other composite in block 40. For example, a selected volume, such as the volumes described above, may be mixed or blended with a plurality of other batches to achieve a selected volume, such as one to create a selected run of formation of a selected prostheses. Regardless, the blending of a plurality of batches may substantially homogenize each of the batches into a selected batch. Therefore, a selected number of prostheses may each have a substantially similar characteristic and can be tested or relied upon for including that characteristic.

Figure 2:
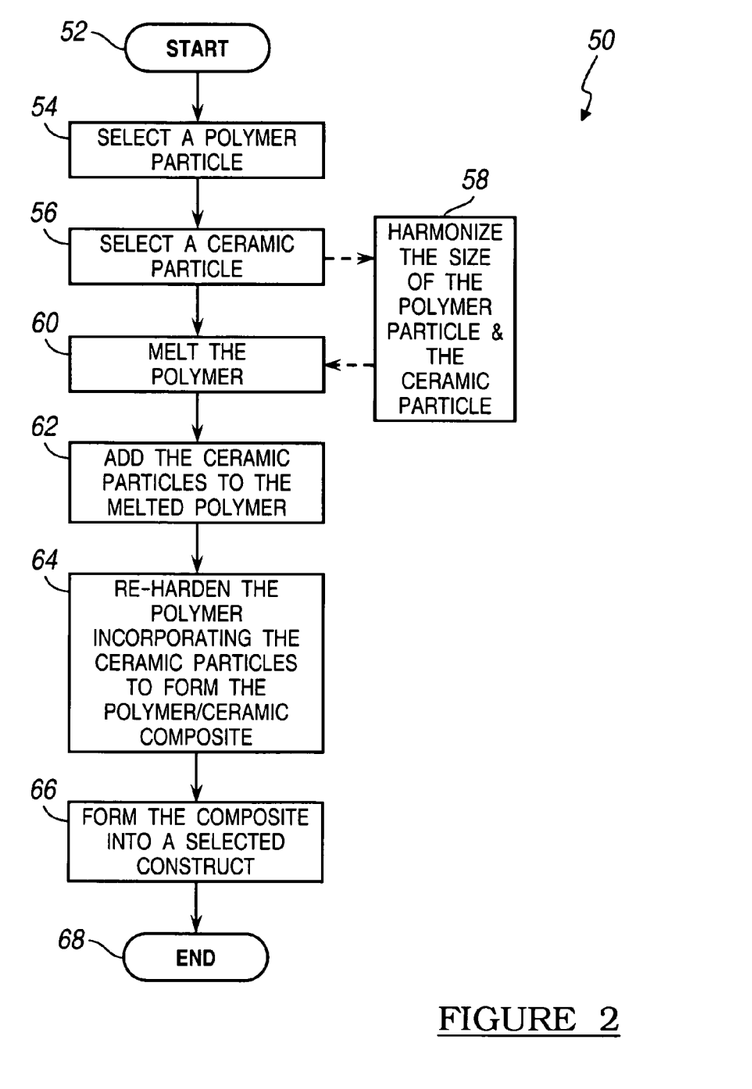
FIG. 2 is a diagrammatic flow chart for forming a polymer/ceramic composite according to various embodiments.

With reference to FIG. 2, a method of forming a polymer/ceramic composite according to various embodiments is illustrated in the flow chart 50. Generally, the method starts at block 52. The method 50 may include steps similar to the method 10 illustrated in FIG. 1. Therefore, in block 54 a polymer may be selected. As discussed above, the selected polymer may be any appropriate polymer, such as a polylactic, polyglycolic and acid combinations thereof, including that sold under the trade name Lactosorb®. Other appropriate polymers may also be selected in block 54. Further, the polymer selected in block 54 may be substantially bioabsorbable and/or biocompatible polymer. As is known in the art, the Lactosorb® material will generally absorb into an anatomy, such as a human anatomy, at a selected rate. Nevertheless, the polymer selected in block 54 may be a substantially non-absorbable polymer, such that it retains a selected shape and character over a long period of time. Further, the polymer selected in block 54 may include various characteristics, such as a viscosity, density, polymer life, and the like. The various characteristics of the polymer may also include a particle size. As discussed above, the particle size may generally include a high aspect ratio or may be obtained or ground to any selected size. Therefore, the polymer selected at block 54 may include various characteristics, either in a raw or partially processed state.

Selecting a ceramic particle may occur in block 56. The selected ceramic particle may be any appropriate ceramic, such as tricalcium phosphate, tetracalcium phosphate, calcium carbonate, calcium sulfate, titanium oxide, alumina, any appropriate ceramic or combination of ceramics. As discussed above, the ceramic may be chosen, depending upon various characteristics of the ceramic itself or the final composite. Further, the ceramic chosen in block 56 may include various characteristics, such as a particle size, density, porosity, and the like. Also, a volume or mass of the ceramic particles may be chosen to mix with a selected amount of the polymer particles.

The particle size of the polymer chosen in block 54 and/or the ceramic chosen at block 56 may be generally harmonized in block 58. As discussed above, the particle sizes may be harmonized for various reasons, such as assisting in mixing the polymer with the ceramic or in achieving a selected dispersion of the ceramic in the polymer. For example, if the ceramic particles are small relative to the polymer particles, the ceramic particles may simply percolate through the collection of the polymer particles and never be dispersed in a final product in a selected manner. However, harmonizing the particle sizes, such as achieving a particle ratio of about five to one to about twenty to one between the polymer and the ceramic may assist in forming a selected composite. Nevertheless, the harmonizing of the particle sizes is optional and not required.

Once the particle sizes are harmonized in block 58, the polymer may be melted in block 60. The polymer may be melted in block 60 in any appropriate manner. Nevertheless, generally the polymer may be melted in a substantially non-degrading manner. Melting the polymer is a nondegrading manner may be melting the polymer to maintain a selected characteristic. For example, the polymer, selected at block 54 may include a selected molecular length or molecular weight. This molecular weight may be any appropriate molecular weight and may depend upon the polymerization of the polymer or the selected polymer chosen. Regardless, melting the polymer at block 60 may be done in a manner to maintain the polymer length of the polymer selected at block 54. Also, a selected viscosity of the polymer selected in block 54 may be maintained when melting the polymer at block 60. It will be understood that various other characteristics may be maintained, such as a final matrix structure, porosity, etc., when melting the polymer at block 60 and these are merely exemplary. Regardless, the polymer may be melted to allow an infiltration or mixing of the ceramic particles selected at block 56.

The ceramic particles may then be added to the melted polymer at block 62. The ceramic particles may then be mixed with the melted polymer in any appropriate manner. For example, an agitation, such as a kneading, may be used to disperse the ceramic particles throughout the melted polymer. As discussed above, the polymer maintains a selected characteristic and therefore dispersing the ceramic particle through the mass of the polymer maintains the characteristic of the polymer while intermixing the ceramic particles therewith.

Once the ceramic particles are mixed with the melted polymer, the melted polymer may be rehardened in block 64 to form the polymer/ceramic composite. Further, as discussed above, various batches of the polymer/ceramic composite formed by mixing the ceramic particles in the melted polymer may be blended together to form a substantially large batch for forming a plurality of selected members.

Once the polymer/ceramic composite is rehardened at block 64, it may be used to form a selected construct in block 66. Similar to the construct described above, the polymer/ceramic composite may be used to form a prosthesis, an implant, or any appropriate member. Nevertheless, the polymer/ceramic composite may be used in any appropriate manufacturing process, such as injection molding, extruding or poltruding, casting, or any appropriate manufacturing process. As discussed above, the polymer/ceramic composite may be formed using any generally known manufacturing technique and may not require a special manufacturing technique. Finally, the method 50 may end at block 68.

Figure 3:
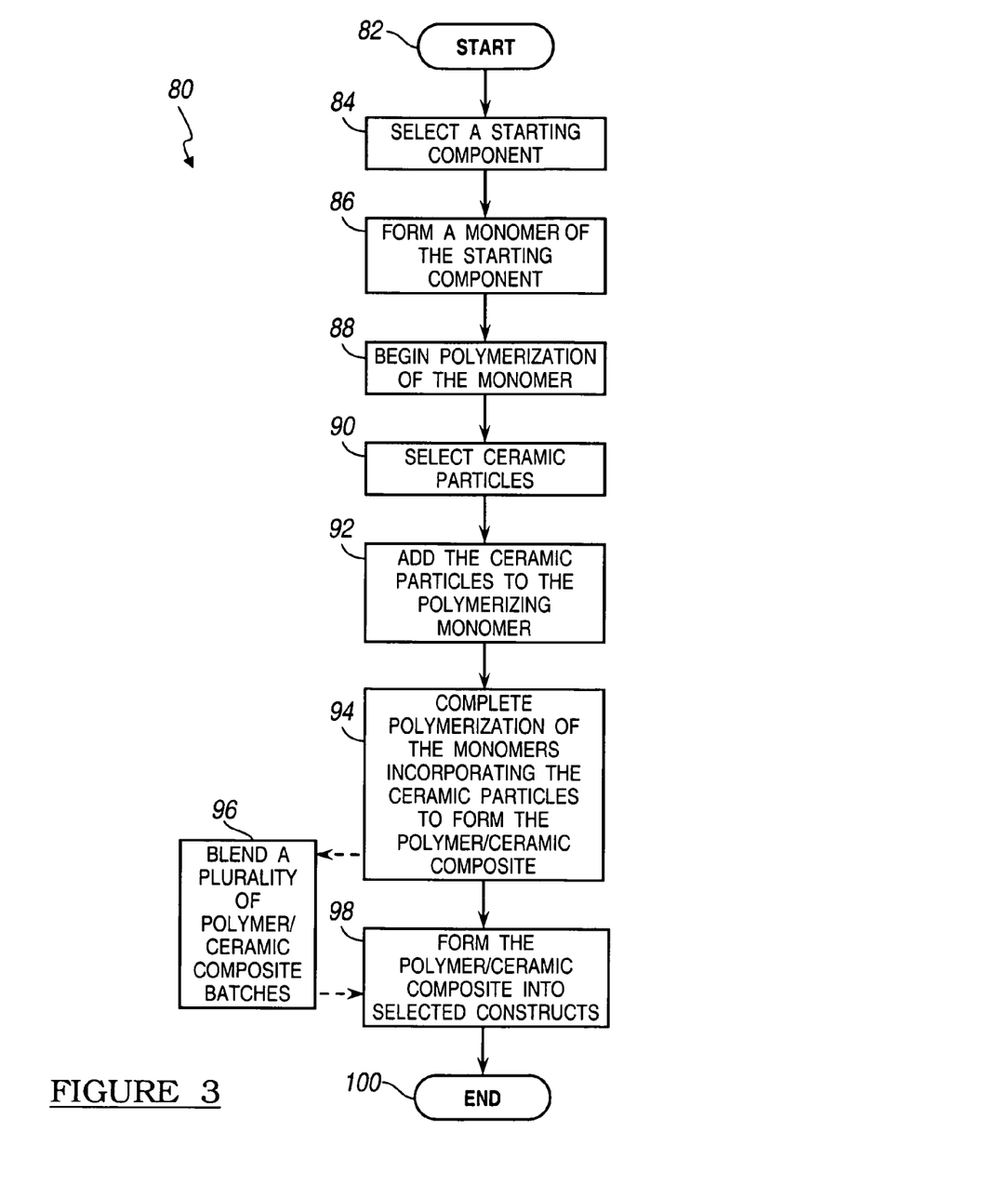
FIG. 3 is a diagrammatic flow chart for forming a polymer/ceramic composite according to various embodiments.

Regarding FIG. 3, a method 80 for forming a polymer/ceramic composite is illustrated. The method 80 may form the polymer/ceramic composite through a generally polymerizing manner that starts in block 82. A starting component, such as a component used to form a polymer, may be selected in block 84. The component selected in block 84 may either be a selected monomer or may be starting components, from which a monomer may be formed to form the polymer. One skilled in the art will understand that a polymer is generally formed of a plurality of monomers bonded together over a selected length or total molecular weight. If the starting component is a starting material, a monomer may be formed in block 86. Nevertheless, it will be understood that the starting component may be a monomer and the formation of a monomer may not be required in block 86.

Regardless, polymerization of the monomers may be begun in block 88. Polymerization may occur according to any appropriate manner, such as with a chemical catalyst or a physical catalyst to begin polymerization. Regardless, the polymerization of the monomers may begin to form a polymer of an appropriate or selected molecular weight or the like. A ceramic particle may be selected in block 90. As discussed above, the ceramic particle selected in block 90 may be any appropriate selected particle, including those listed above. Likewise, the polymer formed in block 88 or having been begun to be formed in block 88 may be any appropriate polymer, such as a bioabsorbable and/or biocompatible polymer that may not be bioabsorbable.

After the ceramic particle is selected in block 90, it may be added to the polymerizing monomer in block 92. The ceramic particles may be added to the polymerizing monomer at any appropriate step in the polymerization. For example, the rate of polymerization may be known and the ceramic particles selected in block 90 may be added to the polymerizing monomers in block 92 at any appropriate time in the polymerization process. For example, it may be selected to add the particles selected in block 90 to the polymerizing monomers at about 1% to about 99% of complete polymerization. Nevertheless, the ceramic particles may be added to the polymerizing monomers in any appropriate time, such as about 25% to about 75% of complete polymerization, also the ceramic particles can be added when the monomer is about 50% completely polymerized to achieve the selected characteristic. Also, complete polymerization may generally be understood to be equilibrium of the polymerization reaction.

For example, it may be selected to add the ceramic particles and a selected step in the polymerization to achieve a selected dispersion of the ceramic particles in the final polymer product. Therefore, the timing of adding the ceramic particles may be chosen depending upon the amount of dispersion, the density of the particles selected in the final product, and the like.

Once the ceramic particles are added, the polymerization of the monomers may be completed in block 94. The completion of the polymerization increases the molecular weight of the polymer, while incorporating the ceramic particles into the final polymer matrix forming the composite. Therefore, the polymer/ceramic composite may be formed during the actual polymerization of the monomers to form the polymer.

The batch of the polymer/ceramic composite formed during the polymerization may be blended with a plurality of other batches in block 96. As discussed above, such blending may create a substantially homogenous volume of the polymer/ceramic composite for forming a selected number of members, such as implants, prostheses, and the like. Nevertheless, it will be understood that a single batch may be formed for various purposes.

Also, the polymer/ceramic composite may be formed into any appropriate construct in block 98. As discussed above, the construct may be formed at any appropriate manner, such as with injection molding, extruding, poltruding, or any appropriate processing method. The polymer/ceramic composite may be formed into a construct in any appropriate manner and may not require specialized processing steps. Finally, the method may end in block 100.

As discussed above, the polymer/ceramic composite may be formed into any appropriate construct, such as a prosthesis or any appropriate member. Regardless, the polymer/ceramic composite may generally include a selected dispersion of ceramic particles in a polymer composite.

Figure 4:
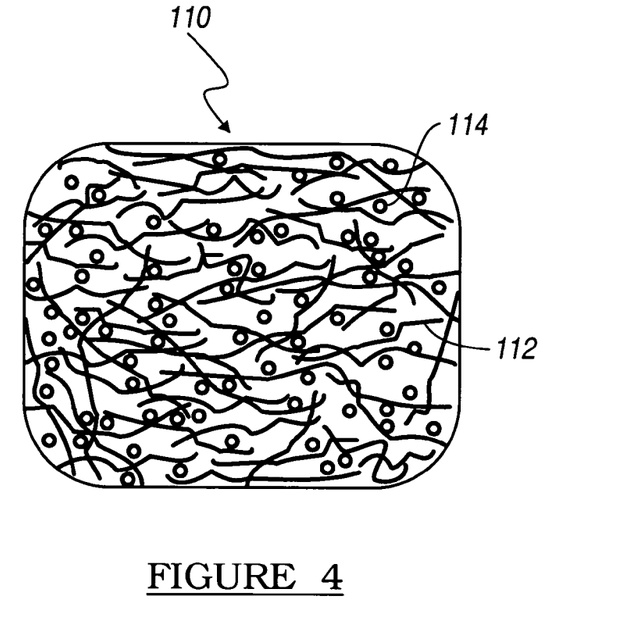
FIG. 4 is an diagram illustrating an exemplary member.

With reference to FIG. 4, a member 110 may define or be an example of any appropriate member, such as a bone filling member. The member 110 may include a plurality of the polymer structures 112 that form a matrix in which a ceramic particle 114 or a plurality of the ceramic particles 114 is dispersed. The ceramic particles 114 may provide or enhance a selected characteristic of the polymer matrix 112. As discussed above, the ceramic particles 114 may increase a hardness or wear characteristic of the polymer matrix 112 of the member 110 for appropriate reasons. As discussed above, the polymer 112 and/or the ceramic particles 114 may be substantially bioabsorbable and/or biocompatible. If both the particle and the polymer matrix 112 are substantially bioabsorbable, then over time both the ceramic particles 114 and the polymer matrix 112 may be absorbed into an anatomy. The absorbed portion may then be replaced with a natural portion, such as a bony ingrowth. Regardless, the ceramic particles 114 may increase a wear characteristic of the member 110, such that the member 110 is more able to substantially mimic a characteristic of a bony portion, such as a hardness, a bearing, or the like. It will be understood that the density of the ceramic particles 114 may be formed in the member 110 according to various methods, such as adding a higher volume of the ceramic particles to a mixture to form the composite or by decreasing the volume of the polymer relative to the ceramic particles. Regardless, the member 110 may be formed according to various embodiments, such as those described above, to provide for a polymer/ceramic composite for various purposes.

The member 100 may then be implanted in any appropriate manner. For example, the member 100 may be formed to fill a specific void. As discussed above, various methods, such as injection molding, may be used to form a selected construct. Therefore, a unique or custom mold may be used to form the injection mold for a selected implant.

Alternatively, the member 100 may be any appropriate implant. For example, the member 100 may be formed into an anchor to be used as a suture anchor or a soft tissue anchor. Regardless, the member 100 may be formed into any appropriate construct for various purposes.

The composites, such as the member 100, may be used for various applications. For example the composite may be used as a bone filler or bone replacement. When a tumor is replaced it may be desirable to replace the resected bone to allow new bone ingrowth into the area. Nevertheless, the composite including various characteristics of all of the materials used to form the composite can be positioned in substantially a single location in the spine, knee, hip, craniofacial, shoulder, extremities, etc.

The composite could also be used for various procedures. For example, a bone plug or fill member could be formed to fill a void in the anatomy. Also, the composite can be used to form various anchors, such as suture or tissue anchors. The composite can also be used to form structural members such as bone plates, interference screws, implants, bone pins, vertebral replacements and others.

The description is merely exemplary in nature and, thus, variations that do not depart from the gist of the disclosure are intended to be within the scope of the teachings. Such variations are not to be regarded as a departure from the spirit and scope of the teachings.

What is claimed is:

1. A method of forming a ceramic and polymer composite for positioning in the anatomy, comprising:
   selecting ceramic particles of a selected size;
   selecting polymer particles of a selected size;
   harmonizing the selected sizes of the polymer particles and of the ceramic particles, wherein the selected size of the polymer particles is at least 0.5 times the selected size of the ceramic particles;
   dissolving the polymer particles in a selected solvent;
   forming a slurry of the dissolved polymer particles and the ceramic particles;
   removing the solvent from the slurry in an amount to cause the slurry to solidify, including adding the slurry to an extraction bath, including a medium that is miscible with the solvent, precipitating the polymer as the solvent is extracted, and changing the extraction bath; and
   forming an implant of the solid.

2. The method of claim 1, wherein selecting polymer particles includes selecting a polymer material from a group comprising a resorbable polymer, a non-resorbable polymer, or combinations thereof.

3. The method of claim 1, wherein selecting ceramic particles includes selecting a ceramic material from a group comprising a resorbable ceramic, a bio-compatible ceramic, a bio-active ceramic, antibiotics, proteins, pharmaceuticals, or combinations thereof.

4. The method of claim 1, wherein the selected solvent is selected from a group comprising an inorganic solvent, an organic solvent, or combinations thereof.

5. The method of claim 1, wherein the selected solvent comprises NMP.

6. The method of claim 5, further comprising:
   selecting ceramic particles comprising a ceramic material including at least one of a hydroxyapatite or a tri-calcium phosphate.

7. A method of forming a ceramic and polymer composite for positioning in the anatomy, comprising:
   selecting ceramic particles of a selected size;
   selecting polymer particles of a selected size;
   harmonizing the selected sizes of the polymer particles and of the ceramic particles;
   dissolving the polymer particles in a selected solvent;
   forming a slurry of the dissolved polymer particles and the ceramic particles;
   removing the solvent from the slurry in an amount to cause the slurry to solidify relative to the ceramic particles, including:
      adding the slurry to an extraction bath, including a medium that is miscible with the solvent,
      precipitating the polymer as the solvent is extracted, and changing the extraction bath; and
   forming an implant of the solid.

8. The method of claim 7, wherein the extraction bath includes water.

9. A method of forming a ceramic and polymer composite for positioning in the anatomy, comprising:
   selecting ceramic particles of a selected size;
   selecting polymer particles of a selected size;
   harmonizing the selected sizes of the polymer particles and of the ceramic particles;
   dissolving the polymer particles in a selected solvent;
   forming a slurry of the dissolved polymer particles and the ceramic particles;
   removing the solvent from the slurry in an amount to cause the slurry to solidify relative to the ceramic particles;
   wherein forming a slurry further includes:
      forming a plurality of batches of the selected ceramic particles and the selected polymer particles;
      blending together the plurality of the batches of the selected ceramic particles and the selected polymer particles; and forming a construct from the blended batches of the selected ceramic particles and the selected polymer particles.

10. The method of claim 1, wherein selecting ceramic particles includes selecting porous ceramic particles.

11. The method of claim 10, wherein forming an implant is selected from a group consisting of extruding, injection molding, casting the solidifying slurry, pultruding, or combinations thereof.

12. The method of claim 1, further comprising forming a dried composite by drying the solidifying slurry of the selected ceramic and the selected polymer to achieve a humidity level.

13. The method of claim 12, wherein the dried composite is the solid that is processed to form the implant.

14. The method of claim 1, wherein forming an implant of the solid includes forming at least one of a bone plate, an interference screw, an implant, a bone pin, a vertebral replacement, a suture anchor, a soft tissue anchor, a bone filler, or combinations thereof.

15. The method of claim 14, wherein the solid is a composite of the ceramic and the polymer formed after removing the solvent from the slurry.

16. The method of claim 1, wherein selecting the ceramic particles includes at least one of selecting a ceramic, and selecting a crystalline particle of at least one of an antibiotic, a protein, a pharmaceutical, or combinations thereof.

17. The method of claim 7, wherein harmonizing includes selecting the particle size of one of the polymer particles and the ceramic particles to be about the same as to about fifty times greater than the particle size of the other of the ceramic particles and the polymer particles.

18. The method of claim 7, wherein harmonizing includes selecting the polymer particle to be about 500 microns or less and the ceramic particles to be about 25 microns or less.

19. The method of claim 7, wherein forming an implant of the solid includes forming at least one of a bone plate, an interference screw, an implant, a bone pin, a vertebral replacement, a suture anchor, a soft tissue anchor, a bone filler, or combinations thereof.

20. The method of claim 7, wherein the solid is a composite of the ceramic and the polymer formed after removing the solvent from the slurry.

21. The method of claim 7, wherein selecting the ceramic particles includes at least one of selecting a ceramic, and selecting a crystalline particle of at least one of an antibiotic, a protein, a pharmaceutical, or combinations thereof.

22. The method of claim 9, wherein harmonizing includes selecting the particle size of one of the polymer particles and the ceramic particles to be about the same as to about fifty times greater than the particle size of the other of the ceramic particles and the polymer particles.

23. The method of claim 9, wherein harmonizing includes selecting the polymer particle to be about 500 microns or less and the ceramic particles to be about 25 microns or less.

24. The method of claim 9, wherein forming an implant of the solid includes forming at least one of a bone plate, an interference screw, an implant, a bone pin, a vertebral replacement, a suture anchor, a soft tissue anchor, a bone filler, or combinations thereof.

25. The method of claim 9, wherein the solid is a composite of the ceramic and the polymer formed after removing the solvent from the slurry.

26. The method of claim 9, wherein selecting the ceramic particle includes at least one of selecting a ceramic, and selecting a crystalline particle of at least one of an antibiotic, a proteins, a pharmaceutical, or combinations thereof.

27. A method of forming a ceramic and polymer composite for positioning in the anatomy, comprising:
   selecting ceramic particles of a selected size;
   selecting polymer particles of a selected size;
   harmonizing the selected sizes of the polymer particles and of the ceramic particles, wherein the selected the size of the polymer particles is less than about six times the selected size of the ceramic particles;
   dissolving the polymer particles in a selected solvent;
   forming a slurry of the dissolved polymer particles and the ceramic particles;
   removing the solvent from the slurry in an amount to cause the slurry to solidify relative to the ceramic particles; and
   forming an implant of the solid;
   wherein removing the solvent includes
      adding the slurry to an extraction bath, including a medium that is miscible with the solvent,
      precipitating the polymer as the solvent is extracted, and
      changing the extraction bath.

28. A method of forming a ceramic and polymer composite for positioning in the anatomy, comprising:
   selecting ceramic particles of a selected size;
   selecting polymer particles of a selected size wherein at least one of the selected or formed size of the polymer particles is less than about six times the selected size of the ceramic particles and the size of the polymer particles to be at least 0.5 times the selected size of the ceramic particles;
   selecting or forming the selected size of the ceramic particles and the polymer particles such that the ceramic particles disperse in a selected manner to allow forming a composite of the polymer and the ceramic;
   dissolving the polymer particles in a selected solvent;
   forming a slurry of the dissolved polymer particles and the ceramic particles;
   removing the solvent from the slurry in an amount to cause the slurry to solidify and form the composite; and
   forming an implant of the composite.

29. The method of claim 28, further comprising:
   forming a plurality of batches of the composite; and
   blending together the plurality of the batches of the composite;
   wherein forming an implant of the composite is forming an implant from the blended batches of the composite.

* * * * *